United States Patent [19]

Seltzer

[11] Patent Number: 4,694,831

[45] Date of Patent: Sep. 22, 1987

[54] MASSAGE FOOTWEAR

[76] Inventor: Charles J. Seltzer, 17 Autumn Dr., Danbury, Conn. 06810

[21] Appl. No.: 887,982

[22] Filed: Jul. 25, 1986

Related U.S. Application Data

[63] Continuation of Ser. No. 568,039, Jan. 4, 1984, abandoned.

[51] Int. Cl.[4] .............................................. A61F 5/14

[52] U.S. Cl. ................................ 128/582; 128/62 R; 36/11.5; 36/43

[58] Field of Search ..................... 128/25 B, 62 R, 67, 128/329 A, 582; 36/43, 44, 11.5

[56] References Cited

U.S. PATENT DOCUMENTS

| | | | |
|---|---|---|---|
| 3,722,113 | 3/1973 | Birkenstock | 36/43 X |
| 4,109,661 | 8/1978 | Fukuoka | 128/582 |
| 4,271,605 | 6/1981 | Raczka | 36/28 |
| 4,345,387 | 8/1982 | Daswick | 36/43 |
| 4,378,007 | 3/1983 | Kachadowian | 128/57 |

FOREIGN PATENT DOCUMENTS

| | | | |
|---|---|---|---|
| 1509688 | 6/1969 | Fed. Rep. of Germany | 128/25 B |
| 3037435 | 4/1982 | Fed. Rep. of Germany | 128/25 B |
| 3103502 | 8/1982 | Fed. Rep. of Germany | 128/25 B |

*Primary Examiner*—Richard J. Apley
*Assistant Examiner*—J. Welsh
*Attorney, Agent, or Firm*—Alfred E. Miller

[57] ABSTRACT

Footwear with an inner sole having upwardly projecting raised flat foot support platforms with foot stimulating, dome-shaped, spaced massage bumps, and non-specific rounded projections on the areas of the inner sole not occupied by the platforms, and the platforms having a lightly stippled surface on the areas on said platforms not occupied by the massage bumps for preventing slippage of the foot when said foot wear article is worn.

5 Claims, 5 Drawing Figures

MASSAGE FOOTWEAR

This application is a continuation of U.S. Ser. No. 568,039, filed Jan. 4, 1984 now abandoned.

The present invention relates to all types of footwear, especially to sandals, athletic, and casual shoes, which are provided with an inner sole having upwardly projecting bumps for massaging the underside of the foot, and it generally provides the wearer with continuous stimulation of the soles of the feet, and has a beneficial effect on the leg and foot muscles and internal organs of the wearer, particularly as relates to the enhancement of circulation in the lower extremities.

Sandals, and other types of footwear, having foot massaging means, are shown in U.S. Pat. No. 3,859,727 to Nakamoto, U.S. Pat. No. 3,722,113 to Bergenstock, and U.S. Pat. No. 4,095,353 to Foulds. However, none of these patents disclose the present arrangement having, a heel support platform, an arch support platform, and a toe support platform, all of which have lightly stippled surfaces and are provided with massage bumps that are arranged on both specific and general pressure and stimulation points. These points are designed so as to positively affect the lower terminus of internal-lines—commonly called meridians which regulate the normal flow of energy throughout the body. In accordance with Oriental medical theory, such as Chinese, developed over centuries, each meridian is linked with one of the major organs of the body, which includes the heart, lungs, liver, stomach, eyes, ears, and reproductive organs. The modern, functional basis for this theory has evolved into the science of acupressure and the related procedure of acupuncture. Acupressure was originally based on the belief that there is a stream of vital life-force energy, called ch'I, flowing throughout our bodies. A low-level energy flow has since been proven to exist through the use of sophisticated modern medical instruments which measure electrical nerve and muscle outputs. This energy circulates through the twelve primary meridians starting with the lungs which draw our breath every twenty-four hours. However, when this energy is blocked, an excess of energy develops in that organ. If the energy flow circulates too freely, the organs will suffer from deficiency. As a result, in either case, illness, pain and body dysfunction may occur. Thus, an acupressure application, which occurs by walking in footwear that is capable of effectively massaging the soles of feet, works to stimulate the appropriate meridians and to bring the so-called life-force energy back into healthful balance and will help enhance or normalize circulation. Consequently, acupressure, as applied in this present invention, works to maintain continuous good health and to aid normal body functioning.

It is an object of the present invention to provide acupressure bumps on raised platforms on the inner sole of footwear for at least twelve key meridians that affect body functions.

Another object of the present invention is to provide footwear or footwear sole inserts—having defined acupressure bumps on raised platforms on the inner sole thereof, which can take the form of an opened or closed toe sandal, or a lace-up or slip-on style athletic or casual shoe, particularly those with an athletic shoe-type bottom sole and/or upper means.

A further object of the present invention is to provide foot support platforms which are either independent or interconconnected.

Further, it is the object of the present invention to provide massage bumps which are rounded in configuration, and which may be of various sizes.

In order that the invention will be more clearly understood, it will now be disclosed in greater detail with reference to the accompanying drawings, in which.

Figure 1:
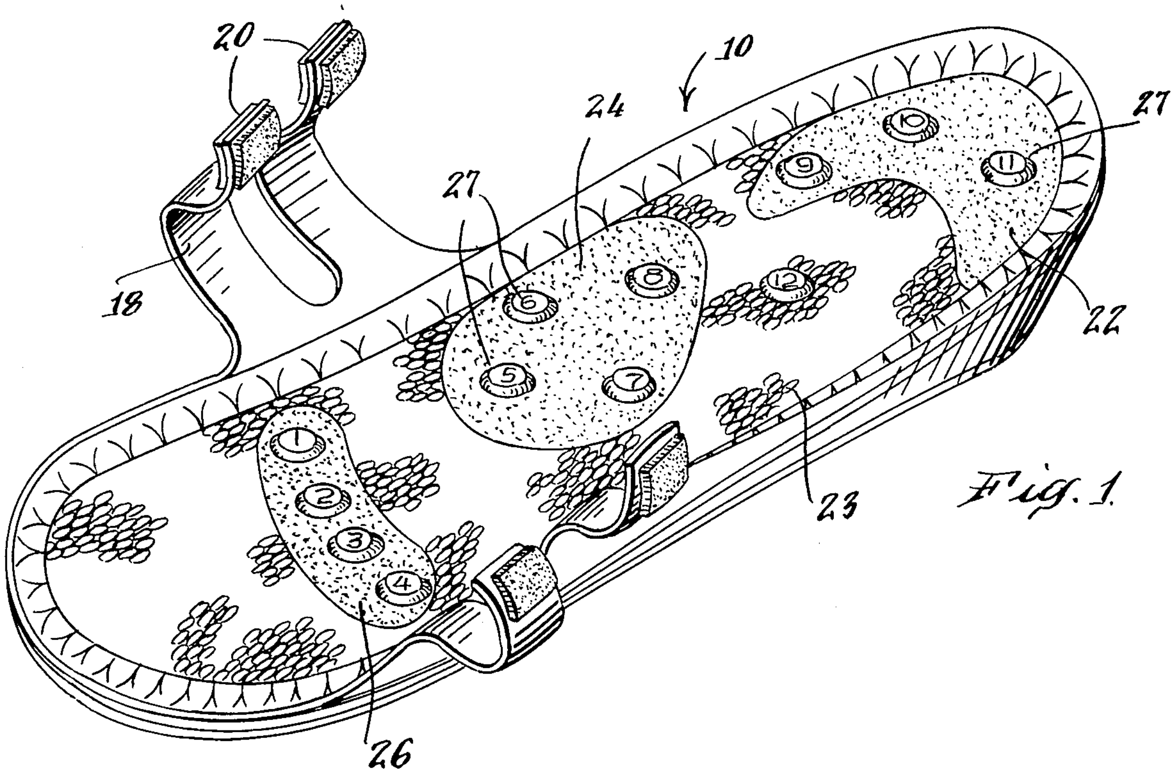
FIG. 1 is a perspective view of the massage footwear constructed in accordance with the teachings of the present invention, and showing independent, non-interconnected placement of the foot support platforms, and the instep straps in open position.
Figure 3:
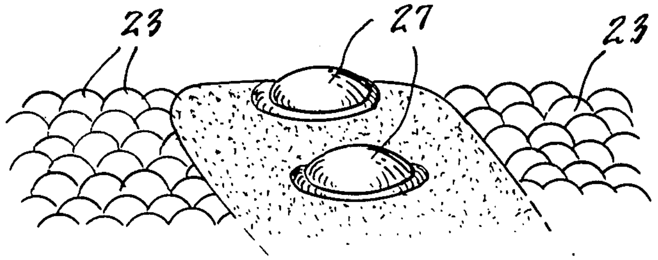
FIG. 3 is an enlarged partial perspective view of the platform and massage bump detail.
Figure 2:
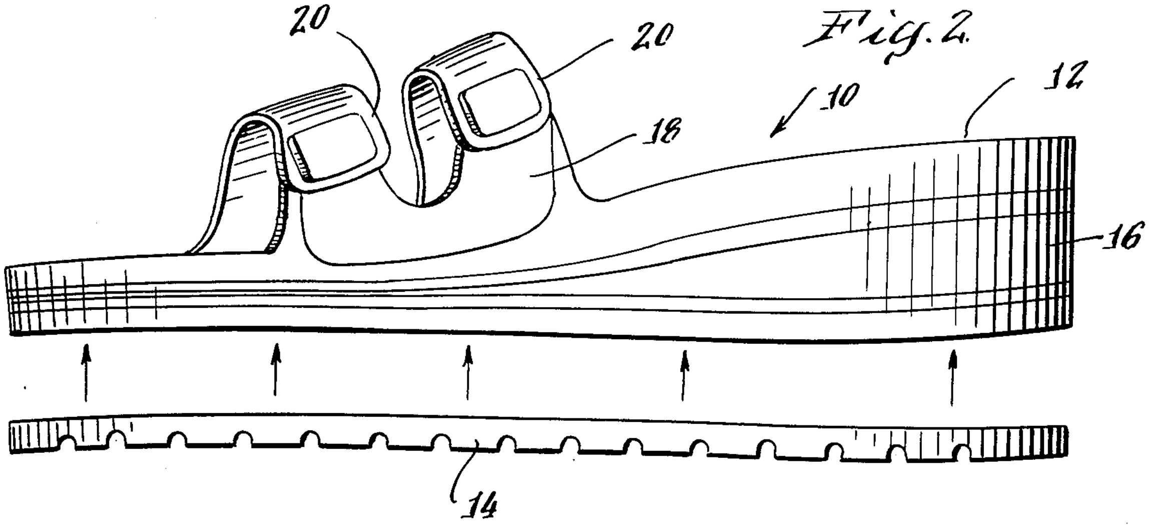
FIG. 2 is a side elevation of the massage footwear showing the instep straps in a closed position.

The footwear article shown in FIGS. 1 and 2 is a massage sandal referred to generally by the numeral 10 provided with an inner sole 12, an outer sole 14, and a wedge-shaped intermediate mid-sole portion 16. Thus, in this example the sandal is provided with a wedge-shaped heel, as clearly shown in FIG. 2.

The sandal 10, as shown, is also provided with upper means such as a pair of strap closures 18 having velcro fasteners 20 at their free ends. FIG. 2 shows the strap closures in their closed position.

As seen in FIG. 1, three separate support platforms 22, 24 and 26 are shown. In this arrangement, support platfrom 22 is provided for the heel of the wearer, while support platform 24 is provided for the arch of the wearer, and support platform 26 accommodates the ball of the foot. It will be noted that each of the support platforms are provided with lightly stippled surfaces, and rounded massage bumps 27, which are numbered 1-11. The stippled surfaces are for the purpose of preventing or limiting slippage of the foot in the sandal 10. Massage bump 12 is provided on the upper surface of the inner sole of the sandal between the heel support platform and the arch or ball of foot support platform. In the present arrangement, the specific application, rounded massage bumps on the platforms, and numbered 1 to 12, are each approximately 3/16" high and ½" in diameter. The bumps are also approximately 1/32" higher than the surrounding platform. It should be noted that the arch, toe ridge and heel contours of the sandal or shoe can be built up from underlying layers, if it is desired to change the configuration of the shoe to better fit foot contours. The upper face of the inner sole of the sandal, other than support platforms 22, 24 and 26, has rounded mounds, bumps, or projections that cover the rest of said inner sole and upon which the other parts of the wearer's sole contacts. These non-specific application massage bumps, in the present arrangement are each approximately 3/16" high and 3/16" in diameter.

Figure 4:
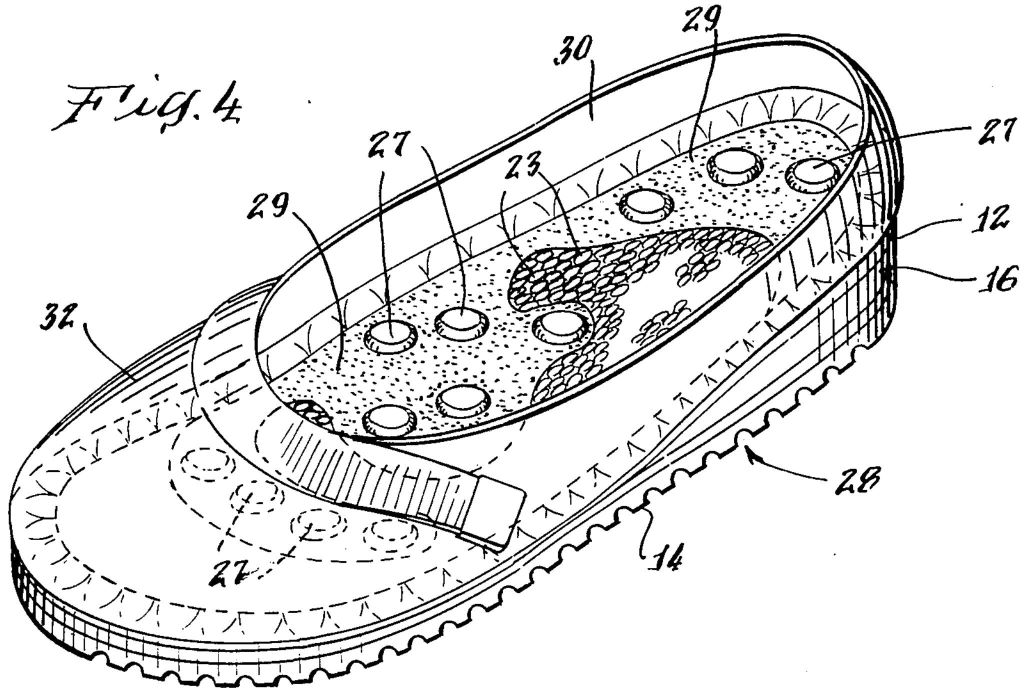
FIG. 4 is a perspective view of an example of a leisure or athletic shoe of the slip-on style having a unitary, interconnected platform with massage bumps.

Referring now to FIG. 4, in which is shown an example of an athletic or casual shoe design of the slip-on style having an upper sole 12, a lower sole 14, and an intermediate wedge 16. The shoe, referred to by the numeral 28, is provided with upper means 30 and a single closure strap 32. The platform construction in FIG. 4 is different than that shown in FIG. 1 in that the heel, arch and ball foot support platforms are all interconnected to form a single or unitary platform, provided with the specific application massage bumps at the appropriate locations, and referred to by the numeral 29.

Figure 5:
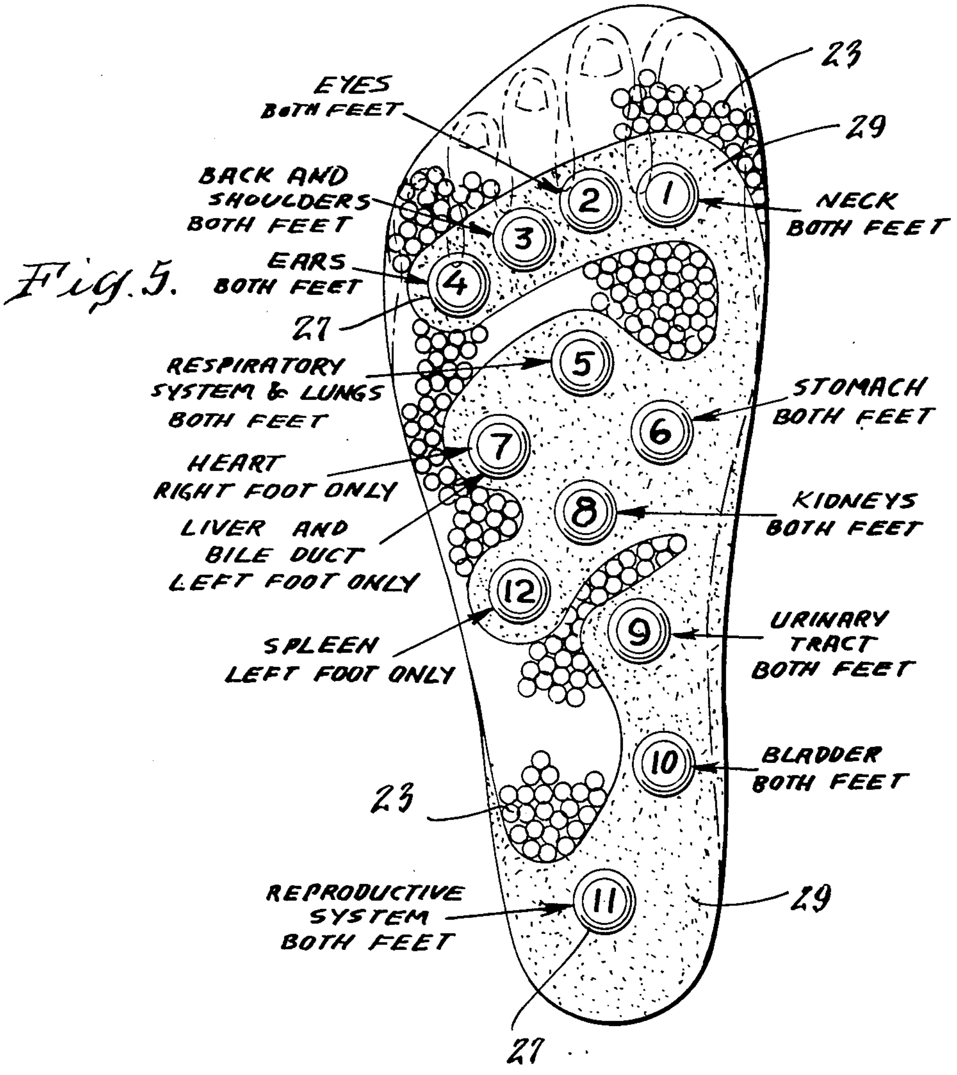
FIG. 5 is a diagrammatic view of the sole of the left foot showing the locations of the terminus points of the acupressure meridians which are engaged by the on-platform massage bumps when wearing my massage footwear.

It should be evident that all the massage bumps 27 and non-specific bumps 23 may engage the sole of the wearer's foot directly if no foot coverings are being worn, or indirectly if foot coverings, such as socks, are worn by the person wearing the massage footwear. FIG. 5 is a diagrammatic showing of the left foot of the wearer with the massage bumps 1–12 placed in their location on the sole of the wearer's foot. These massage bumps are indicated as 1–12 together with legends specifying the body organs that are affected, according to theory previously disclosed herein by the acupressure massage of those areas by means of applicant's massage bumps. Thus, as the wearer walks, there is a continuous stimulation of the soles of the feet, which encourages circulation to the lower extremities, thereby enhancing the flow of freshly oxygenated blood to, especially, the leg and foot muscles. This will speed recovery from muscle fatigue, can help strengthen the internal organs of the body, and provides an improvement in overall health of the wearer.

What is claimed is:

1. A footwear article having an outer sole provided with an inner surface normally facing the underside of a human foot and an upper closure means for said footwear article and attached to opposite marginal edges thereof, at least three raised flat foot support platforms on said inner surface, said inner surface other than the portion supporting said platforms being provided with a plurality of non-specific rounded projections located on substantially all the areas of said inner surface not occupied by said platforms, said platforms having a plurality of spaced, foot stimulating, dome-shaped massage bumps, each of said bumps having a greater diameter than height, and said platforms having a flat, lightly stippled surface on each of said platforms in the areas not occupied by said massage bumps for preventing slippage of the foot when said footwear article is worn, said platforms with massage bumps thereon supporting the ball, mid-sole, arch and heel of the wearer's foot, the locations of said massage bumps being selected to engage the underside of the wearer's foot either directly or indirectly to cause continuous stimulations of the sole of the foot thereby providing an improvement in circulation and in the overall health of the wearer.

2. A footwear article as claimed in claim 1 having at least 11 massage bumps with relatively large rounded surfaces.

3. A footwear article as claimed in claim 1 wherein three separate foot support platforms are provided on said inner surface, and which are adapted to support the toes, the heel, the arch and/or the ball of the foot, respectively, or in any combination thereof.

4. A footwear article as claimed in claim 1 wherein said massage bumps on said platforms are each approximately 3/16" high and ½" in diameter.

5. A footwear article as claimed in claim 1 wherein said non-specific rounded projections are each approximately 3/16" high and 3/16" in diameter.

* * * * *